US008980826B2

(12) United States Patent
McMichael

(10) Patent No.: US 8,980,826 B2
(45) Date of Patent: Mar. 17, 2015

(54) METHOD OF TREATING CHRONIC OBSTRUCTIVE PULMONARY DISEASE

(71) Applicant: Beech Tree Labs, Inc., Delanson, NY (US)

(72) Inventor: John McMichael, Delanson, NY (US)

(73) Assignee: Beech Tree Labs, Inc., Delanson, NY (US)

(*) Notice: Subject to any disclaimer, the term of this patent is extended or adjusted under 35 U.S.C. 154(b) by 0 days.

(21) Appl. No.: 13/778,690

(22) Filed: Feb. 27, 2013

(65) Prior Publication Data
US 2013/0225480 A1 Aug. 29, 2013

Related U.S. Application Data

(60) Provisional application No. 61/603,701, filed on Feb. 27, 2012.

(51) Int. Cl.
| A61K 38/00 | (2006.01) |
| A61P 11/00 | (2006.01) |
| A61P 11/06 | (2006.01) |
| A61K 38/16 | (2006.01) |
| A61K 48/00 | (2006.01) |
| C07K 1/00 | (2006.01) |
| C07K 14/00 | (2006.01) |
| C07K 17/00 | (2006.01) |
| C07K 16/00 | (2006.01) |
| C12N 15/00 | (2006.01) |
| G01N 33/564 | (2006.01) |
| A61K 31/7088 | (2006.01) |
| A61K 45/00 | (2006.01) |
| A61K 9/00 | (2006.01) |
| A61K 31/713 | (2006.01) |

(52) U.S. Cl.
CPC ............ *A61K 38/164* (2013.01); *A61K 31/7088* (2013.01); *A61K 45/00* (2013.01); *A61K 9/00* (2013.01); *A61K 31/713* (2013.01); *A61K 9/006* (2013.01)
USPC ........... 514/1.5; 514/1.7; 514/21.2; 514/44 R; 530/350; 530/362; 435/455; 436/508

(58) Field of Classification Search
None
See application file for complete search history.

(56) References Cited

U.S. PATENT DOCUMENTS

| 5,576,289 | A | 11/1996 | McMichael |
| 5,726,160 | A | 3/1998 | McMichael |
| 5,736,508 | A | 4/1998 | McMichael |
| 5,798,102 | A | 8/1998 | McMichael et al. |
| 5,948,768 | A | 9/1999 | McMichael et al. |
| 5,955,442 | A | 9/1999 | McMichael |
| 6,096,721 | A | 8/2000 | McMichael |
| 6,100,244 | A * | 8/2000 | McMichael ................ 514/44 R |
| 6,303,127 | B1 | 10/2001 | McMichael et al. |
| 6,998,121 | B2 | 2/2006 | McMichael |
| 7,196,058 | B2 | 3/2007 | McMichael et al. |
| 7,629,312 | B2 | 12/2009 | McMichael |
| 2003/0032614 | A1* | 2/2003 | McMichael ................ 514/44 |
| 2008/0182789 | A1* | 7/2008 | McMichael ................ 514/12 |
| 2009/0202587 | A1* | 8/2009 | Paterson et al. ............ 424/200.1 |
| 2010/0144602 | A1 | 6/2010 | McMichael |

FOREIGN PATENT DOCUMENTS

WO WO-0064487 A2 11/2000

OTHER PUBLICATIONS www.medical-dictionary.thefreedictionary.com/subject, "Suject", 2 pages, accessed on Sep. 3, 2014.*
Horohov et al., "The use of streptolysin O (SLO) as an adjunct therapy for *Rhodococcus equi* pneumonia in foals," *Veterinary Microbiology*, 154: 156-162 (2011).
International Search Report in corresponding PCT/US2013/027929 mailed May 13, 2013.
Written Opinion in corresponding PCT/US2013/027929 mailed May 13, 2013.
Razin et al., "Protein Kinases C—β and C—ε Link the Mast Cell High-Affinity Receptor for IgE to the Expression of *c—fos* and *c—jun*," Proc. Natl. Acad. Sci. (USA), 91:7722-7726 (1994).

* cited by examiner

*Primary Examiner* — James H Alstrum Acevedo
*Assistant Examiner* — Thea D'Ambrosio
(74) *Attorney, Agent, or Firm* — Marshall, Gerstein & Borun LLP

(57) ABSTRACT

The present invention relates to a method of promoting bronchodilation by administration of streptolysin O to a subject in need thereof.

10 Claims, No Drawings

METHOD OF TREATING CHRONIC OBSTRUCTIVE PULMONARY DISEASE

This application claims the benefit of U.S. Provisional Application Ser. No. 61/603,701 filed Feb. 27, 2012, the disclosure of which is hereby incorporated by reference.

BACKGROUND OF THE INVENTION

Streptolysin O is one of a group of filterable hemolysins derived from Group A beta-hemolytic streptococci. Specifically, streptolysin O is a 60 kD peptide which is hemolytic in its reduced state but is inactivated upon oxidation. Streptolysin O is used in the art generally as an analytical reagent for permeabilizing cells. See, e.g., Razin et al., Proc. Nat'l. Acad. Sci. (USA), 91:7722-7726 (1994).

U.S. Pat. No. 5,576,289 is directed to methods of treating motor deficit symptoms in diseases such as autism, multiple sclerosis and Tourette's Syndrome by administration of streptolysin O.

U.S. Pat. No. 5,736,508 is directed to methods of treatment of scar tissue including the appearance of fine lines, wrinkles and stretch marks by administration of streptolysin O.

U.S. Pat. No. 5,798,102 is directed to methods of treating symptoms of cardiomyopathy comprising administering a composition comprising beta-amyloid, streptolysin O and growth hormone. U.S. Pat. No. 6,303,127 is similarly directed to methods of treating symptoms of cardiomyopathy in non-human animals, Parkinson's Disease and degenerative liver disease including cirrhosis by administration of a composition comprising beta-amyloid, streptolysin O and growth hormone.

U.S. Pat. No. 6,998,121 is directed to methods of treating connective tissue disorders in animals such as Dupuytren's contracture, scleroderma, Peyronie's disease, mastitis in animals, and claudication due to peripheral arterial disease by the administration of streptolysin O.

U.S. Pat. No. 7,196,058 is directed to methods of alleviating symptoms of reproductive fibrosis conditions in a subject comprising administering effective amounts of streptolysin O. Representative fibroses include uterine fibrosis, fallopian tube fibrosis. The patent also discloses the property by which streptolysin O interacts with the CD44 receptor and inhibits CD44 mediated processes.

U.S. Pat. No. 7,629,312 relates to a method of treatment of connective tissue disorders including tendonitis, claudication resulting from peripheral artery disease, Duputren's contracture, Peyronie's Disease, scleroderma, and connective tissue disorders associated with chronic mastitis by administration of streptolysin O. The patent also discloses the property by which streptolysin O interacts with the CD44 receptor and inhibits CD44 mediated processes.

US 2003/0032614 discloses methods for the treatment of respiratory congestion comprising the administration of a polynucleic acid such as DNA. The publication discloses the treatment of equine heaves by the administration of synthetic DNA. The publication also discloses the sublingual administration of DNA with and without streptolysin O for the treatment of radiation induced mucositis although it was reported that it could not be determined whether the incorporation of streptolysin O improved the therapeutic results.

US 2008/0182789 discloses methods of treating idiopathic pulmonary fibrosis which is a progressive and fatal lung disease characterized by progressive fibrotic changes to the lung tissue. The published application disclosed treatment of a subject diagnosed with idiopathic pulmonary fibrosis with sublingual administration of a composition comprising 2 units of streptolysin and 0.3 μg of salmon testicle DNA. Disease progression was arrested and the subject was observed to have stable or improved results on pulmonary function tests.

US 2010/0144602 discloses methods of inhibiting metastatic cancer by the administration of streptolysin O and further discloses the property by which streptolysin O interacts with the CD44 receptor and inhibits CD44 mediated processes.

U.S. Provisional Application No. 61/486,566, filed May 16, 2011, discloses methods of treating disorders associated with sequestered bacteria such as tuberculosis in subjects comprising the step of administering to the subject a combination therapy comprising streptolysin O and antibiotic therapy. Without being bound by any particular theory of invention it is believed that the streptolysin O promotes treatment of the infection by breaking down the abscesses associated with many pathogenic bacteria allowing the antibiotics to have access to the bacteria within the abscess.

The present invention relates to the discovery that Streptolysin O has bronchodilation effects in addition to its other effects relating to fibrosis such as relate to scar healing, fibrotic diseases and treatment of diseases such as tuberculosis associated with sequestered bacteria.

Bronchodilators are substances that dilate the bronchi and bronchioles and by doing so decrease resistance in the respiratory airway and increase airflow to the lungs. They are useful in diseases such as asthma in which an inflammatory response causes obstruction of airflow and bronchospasm. Symptoms of asthma include wheezing, coughing, chest tightness and shortness of breath. Asthma is a chronic obstructive condition but is not considered a chronic obstructive pulmonary disease as this term is used to specifically refer to combinations of disease that are irreversible such as bronchiectasis, chronic bronchitis and emphysema Self, Timothy. Chrisman, Cary. Finch, Christopher. "Applied Therapeutics: The Clinical Use of Drugs, 9th Edition" Philadelphia: Lippincott Williams & Wilkins, 2009. Chapter 22 (Asthma) Unlike these diseases, the airway obstruction in asthma is usually reversible, but if left untreated, chronic inflammation can lead the lungs to become irreversibly obstructed due to airway remodeling.

Asthma affects the bronchi while emphysema affects the alveoli. Asthma like chronic bronchitis, is a disease of the airways. Obstruction to the flow of air is due to inflammation of the airways as well as spasm of muscles surrounding the airways in asthma. The narrowing that results from spasm of the muscles is called bronchospasm. Generally, bronchospasm in asthma is reversible and subsides spontaneously or with the use of bronchodilators. A major component of asthma is inflammation of the airways, and this inflammation causes thickening of the walls of the airways. This inflammation involves different inflammatory cells and mediators than those seen in chronic bronchitis. This may play a role in the choice of anti-inflammatory medications for these similar yet different entities. In many asthmatics, anti-inflammatory medications such as inhaled steroids are required to reduce this inflammation. In long standing asthma, this chronic inflammation can lead to scarring and fixed airway obstruction.

Bronchodilators can also be useful in the treatment of aspects of other pulmonary diseases including chronic obstructive pulmonary diseases (COPDs) which share the common feature of chronic expiratory airflow limitation i.e., persistent slowing of the rate at which exhalation can be achieved. Common COPDs include chronic bronchitis, emphysema and asbestosis and are characterized by respiratory distress but are not associated with aberrant mucous accumulation. Cigarette smoke is the most common cause of COPDs which are also associated with exposure to respirable dusts particularly in workplace environments of those engaged in occupations such as gold and coal mining, textile manufacturing and cement and steel making.

Bronchodilators are either short-acting or long-acting. Short-acting bronchodilators are used in "rescue" inhalers to provide rapid relief from acute bronchoconstriction. Medications such as salbutamol usually take effect within 20 minutes or less and provide temporary relief from asthma symptoms or flare-ups. Some short-acting β-agonists such as salbutamol are specific to the lungs and can relieve bronchospasms without unwanted cardiac (β-1) side effects of non-specific O agonists such as ephedrine or epinephrine.

Long-acting β2-agonists such as salmeterol and formoterol are useful for preventing bronchoconstriction but are not useful for fast relief. Such medications can relieve airway constriction for up to 12 hours and can be taken twice a day with anti-inflammatory medications.

Other compounds such as anticholinergics, psychostimulant drugs that have an amphetamine like mode of action and theophilline act as bronchodilators but their use is limited because of side effects.

Of interest to the present invention are patents directed to the use of DNA in the absence of gene transfer for treatment of respiratory conditions. U.S. Pat. No. 5,726,160 is directed to a method of method for relieving respiratory congestion in a patient, comprising the step of administering sublingually and in a manner so as not to effect gene transfer and expression, a therapeutically effective amount of DNA in a pharmaceutically acceptable vehicle to a patient having a disease characterized by respiratory congestion, wherein said respiratory congestion is a result of an overproduction of viscous mucus or sputum lodged in said patient's respiratory tract, and wherein said method results in the reduced viscosity of said mucus or said sputum such that there is an increase of production and a reduced accumulation of mucus in said patient's respiratory tract.

U.S. Pat. No. 5,955,442 is directed to methods for treating respiratory disease including cystic fibrosis, emphysema, bronchitis and sinusitis by administration of an effective amount of DNA in a manner so as not to effect gene transfer and expression.

U.S. Pat. No. 5,948,768 is directed to methods of treating otitis media by administration of effective amounts of DNA such as by sublingual administration.

U.S. Pat. No. 6,096,721 is directed to a method for treating mucositis of the respiratory tract in a subject comprising the step of administering DNA to the subject.

U.S. Pat. No. 6,100,244 relates to a method for treating respiratory distress by sublingual administration of DNA. More specifically, the patent provides methods for treating symptoms of respiratory distress not associated with aberrant mucous accumulation in a patient, comprising the step of administering in a manner so as not to effect gene transfer an effective amount of DNA in a pharmaceutically-acceptable vehicle to a patient having a disease characterized by respiratory distress not associated with aberrant mucous accumulation including but not limited to diseases such as chronic obstructive pulmonary disease including bronchitis, emphysema and asbestosis as well as asthma. The patent further provides methods for relieving respiratory congestion in a patient as a result of overproduction of viscous mucus or sputum lodged in the patient's respiratory tract due to conditions including mucositis such as caused by radiation comprising the steps of administering in a manner so as not to effect gene transfer a therapeutically effective amount of DNA in a pharmaceutically-acceptable vehicle to a patient having a disease characterized by respiratory congestion, wherein said respiratory congestion is a result of an overproduction of viscous mucus or sputum lodged in said patient's respiratory tract, and wherein said method results in the reduced viscosity of said mucus or said sputum such that there is an increase of production and a reduced accumulation of mucus in said patient's respiratory tract.

Methods of the invention comprise administration to a patient suffering from respiratory distress an effective amount of DNA. The DNA is preferably provided in an amount ranging from about 0.00012 mg to about 0.003 mg and is preferably formulated in a liquid vehicle and provided at a concentration of approximately 0.0006 mg as single drops. A preferred route of administration is sublingual, but other routes, such as subcutaneous, intravenous, intramuscular, and intrathecal are expected to work. DNA for use in the present invention may be prokaryotic DNA or eukaryotic DNA and may be formulated in a number of pharmaceutically-acceptable vehicles, including water, saline, albumin, and dextrose.

Despite the various therapies known to the art for treating bronchoconstriction there remains a need in the art for improved methods of promoting bronchodilation in subjects in need thereof.

BRIEF SUMMARY OF THE INVENTION

The present invention is directed to discovery that administration of streptolysin O (SLO) and biologically active fragments thereof are useful as long-acting agents in promoting bronchodilation and preventing bronchospasm in humans and other mammals including horses and dogs in need thereof. As such SLO, may be administered to those prone to asthma and other conditions characterized by broncho-constriction to relieve such constriction.

Preferred methods of practicing the invention comprise sublingual administration of the SLO in the form of a liquid drop. The SLO can be administered for promoting brochodilation and preventing bronchospasm for any of a variety of conditions but is particularly useful for treatment of asthma including asthma in the absence of such conditions as COPD. The SLO is preferably administered in a liquid vehicle such as those selected from the group consisting of water, saline, albumin, or dextrose. The streptolysin O is preferably administered at a dosage of from 0.0032 to 50 units per day with administration of four doses of 2 units per day being particularly preferred. The SLO can be administered as a holoprotein isolated from streptococci or can be administered as a recombinately produced holoprotein or biologically active fragment with the fragment consisting of amino acid nos. 79-571 of SEQ ID NO: 1 being particularly preferred.

The SLO can be administered alone or in combination with other components such as DNA and other bronchodilators. Preferred dosages of DNA for administration with the SLO range from about 0.00012 mg to about 0.003 mg DNA with dosages of about 0.0006 mg of DNA being particularly preferred.

DETAILED DESCRIPTION OF THE INVENTION

Streptolysin O is one of a group of filterable hemolysins derived from Group A beta-hemolytic streptococci. Specifically, streptolysin O is a 60-kD peptide, which is hemolytic in its reduced state, but is inactivated upon oxidation. Group A streptococci produce streptolysin O. Streptolysin O is used in the art generally as an analytical reagent for permeabilizing cells (e.g. Razin et al., Proc. Nat'l. Acad. Sci. (USA) 91:7722-7726 (1994)).

Streptolysin O may be formulated in a number of pharmaceutically-acceptable excipients including, but not limited to, water, saline, albumin, dextrose or any other pharmaceutically acceptable excipient known in the art. The streptolysin O is preferably administered in an oxidized state and in a dosage amount ranging from about 0.0032 to 50 units (2 units/0.05 ml) per day and is preferably formulated in a liquid vehicle and provided at a concentration of approximately 4 units as a single drop. A single drop of streptolysin O is within the range of 0.05 to 10 units. More preferably, a drop of streptolysin O comprises about 2 units as a single drop. Streptolysin O is more preferably administered in an amount ranging from about 0.01 to 10 units per day or even more preferably administered in an amount ranging from about 0.1 to 8 units per day.

The streptolysin O is, in some embodiments, formulated in a number of pharmaceutically-acceptable carriers or excipients including, but not limited to, water, saline, albumin, dextrose or any other pharmaceutically acceptable excipient known in the art. The precise dose will vary among patients and may readily be determined by those of ordinary skill in the art. In some embodiments, the streptolysin O is administered in a dosage amount ranging from about 0.0032 to 50 units (2 units/0.05 ml) per day and is preferably formulated in a liquid vehicle. A single drop of streptolysin O is within the range of 0.05 to 10 units. In some embodiments, a drop of streptolysin O is in the amount of 2 units as a single drop. In other embodiments, the streptolysin O is more administered in an amount ranging from about 0.01 to 10 units per day. In still other embodiments, the streptolysin O is administered in an amount ranging from about 0.1 to 8 units per day. In other embodiments, the administered dose of streptolysin O is from about 1 unit to about 5 units. In yet other embodiments, the administered dose of streptolysin O is about 2 units. A preferred route of administration is sublingual but other routes, such as bucal, oral drench, sublingual, intradermal, intramuscular, intrathecal, intravenous, inhalation or topical, are also contemplated. For non-human animals such as horses, a preferred mode of administration is by subcutaneous administration at a dosage of 2 units per dose (0.2 cc).

Methods of the invention can use SLO holoprotein having the sequence of SEQ ID NO:1 as set out below or according to one aspect of the invention can comprise a recombinant product comprising amino acids 79-571 of SEQ ID NO:1.
SEQ ID NO:1
Native Amino Acid Sequence of SLO Protein:
MSNKKTFKKYSRVAGLLTAALIIGN-LVTANAESNKQNTASTETTTTNEQPKPESSELT TEK-AGQKTDDMLNSNDMIKLAPKEMPLESAE-KEEKKSEDKKKSEEDHTEEINDKIYS LNYNELEVLAKNGETIENFVPKEG-VKKADKFIVIERKKKNINTTPVDISIIDSVTDRTY PAALQLANKGFTENKPDAVVTKRNPQKI-HIDLPGMGDKATVEVNDPTYANVSTAID NLVN-QWHDNYSGGNTLPARTQYTESMVYSKS-QIEAALNVNSKILDGTLGIDFKSISK GEKKVMIAAYKQIFYTVSANLPNNPAD-VFDKSVTFKELQRKGVSNEAPPLFVSNVAY GRTVFVKLETSSKSNDVEAAFSAALKGT-DVKTNGKYSDILENSSFTAVVLGGDAAEH NKVVT-KDFDVIRNVIKDNATFSRKNPAYPI-SYTSVFLKNNKIAGVNNRTEYVETTSTE YTSGKINLSHQGAYVAQYEILWDEINYD-DKGKEVITKRRWDNNWYSKTSPFSTVIPL GAN-SRNIRIMARECTGLAWEWWRKVIDERD-VKLSKEINVNISGSTLSPYGSITYK Compositions according to the invention can further comprise a pharmaceutically acceptable excipient such as those wherein the pharmaceutically acceptable excipient is selected from the group consisting of proteins, polysaccharides, polylactic acids, polyglycolic acids, polymeric amino acids, amino acid copolymers, and inactive virus particles, antioxidants, chelating agents carbohydrates, dextrin hydroxyalkylcellulose, hydroxyalkylmethylcellulose, stearic acid, oils, saline, glycerol, ethanol, wetting agents, emulsifying agents, pH buffering substances and liposomes. According to one aspect of the invention the pharmaceutically acceptable excipient is a sterile fixed oil.

Additional aspects, features and variations of the invention will be apparent from the entirety of this application, including the detailed description, and all such features are intended as aspects of the invention. It should be understood, however, that the detailed description and the specific examples are given by way of illustration, and that the many various changes and modifications that will be apparent to those familiar with the field of the invention are also part of the invention.

Aspects of the invention described with the term "comprising" should be understood to include the elements explicitly listed, and optionally, additional elements. Aspects of the invention described with "a" or "an" should be understood to include "one or more" unless the context clearly requires a narrower meaning.

The following Examples illustrate the preferred embodiments of the invention and provide evidence of the effectiveness of claimed treatment methods. Numerous improvements and further aspects of the invention are apparent to the skilled artisan upon consideration of the Examples which follow.

Example 1

According to this example a seventy-two-year-old adult presented with a 30+ year history of asthma which had been well-controlled for many years with inhaled steroids/bronchodilator.

Spirometry:

Force vital capacity 1.93 liters or 69% predicted. FEV1 1.33 liters or 63% predicted. FEV1/FVC ratio is 69. Post bronchodilator force vital capacity 2.05 liters or 73% predicted. Post bronchodilator FEV1 is 1.44 liters or 68% predicted. Total lung capacity is 2.69 liters or 57% predicted. Diffusion capacity is 72% predicted. Assessment: 1) Mild obstructive defect. Proportionally decreased FEV1 and FVC and spirometry consistent with restriction. 2) Moderate restrictive defect based on total lung capacity of 57% predicted. 3) Mild decreased diffusion capacity.

Ten months after the original spirometry measurements a physical examination was performed which indicated that the previous bilateral pleural effusions had resolved. There was some pleural thickening in the right lung base, and there was also residual pleural effusion. There were a few areas of slight prominence of the interlobar pleural fissures. There were no focal infiltrates or areas of atelectasis. The cardiomediastinal structures and distribution of the pulmonary vasculature were normal. Therapy was initiated comprising sublingual administration of drops comprising 2 units of streptolysin O and 0.0006 mg of salmon sperm DNA four times daily.

Evaluation by a pulmonologist after 12 months of treatment indicated that the subject's pulmonary function tests prebronchodilator were a little bit suspicious for mild obstruction but postbronchodilator she returned to be within normal limits. Compared to a study done a year prior to treatment with the SLO/DNA composition when the patient was sick and an inpatient at that time her FEV1 improved from 1.33 to 2.05, a 54% improvement and FVC improved from 1.93 to 2.89 a 50% improvement.

Spirometry was then conducted on the subject after a year of treatment: FEV1=2.07 FVC=2.77:

| Spirometry: | 10 Months pre-treatment | 12 Months post-treatment | % Change |
|---|---|---|---|
| FEV1 | 1.33 | 2.05 | +54% |
| FVC | 1.93 | 2.89 | +50% |

The subject was evaluated as suffering from asthma and hyperlipidemia. The subject had done very well and had a good 6 months and rarely used her metered dose inhaler. Lungs were now clear to percussion and auscultation and the pulmonologist did not hear a wheeze on examination. Her asthma was doing very well. Evaluation another year later indicated that the subject was still doing well.

Example 2

According to this example a 68 year old subject presented who was first diagnosed with asthma and recurrent sinusitis/bronchitis at age 45. The subject was initiated on treatment with the SLO and DNA containing sublingual drops according to the method of Example 1 on Day 0. Over ensuing year the subject had only one case of viral sinusitis/bronchitis which never progressed to needing antibiotic treatment. Doing well. The subject used a combination of budesonide and formoterol (Symbicort®) 160/4.5 puffs BID—very little use of rescue meds. She stopped taking drops 2 months at approximately Day 510. Spirometry was conducted at Day 570 as which time the subject started administration of the SLO and DNA composition again.

| Spirometry: | Day 0 | Day 570 | Day 600 |
|---|---|---|---|
| FVC | 2.95 | 3.21 | 3.25 |
| FEV1 | 1.68 | 1.44 | 1.65 (72%, up from 59% predicted) |

Example 3

According to this example a seventy-two-year-old woman presented with adult onset asthma (i.e., chronic asthma with frequent exacerbation.) The subject was treated with the sublingual SLO/DNA drops of Example 1 four times daily and during the following year there was only one episode of sinusitis/bronchitis which was mild and from which the subject recovered quickly. The subject's asthma was well controlled with a blend of gluticasone and salmeterol (Advair® 240/50) BID and there was little use of a rescue inhaler and much better stamina. The subject reported that she felt better than had in years and has been on same medications for year.

Example 4

According to this example a fifty-one-year-old male presented with adult onset asthma; asthma/recurrent sinusitis and was treated with the sublingual SLO/DNA drops of Example 1 four times daily. The subject reported much improved asthma control and much decreased episode of sinusitis.

Example 5

According to this example a fifty-eight-year-old male presented with longstanding asthma; extremely thick mucus; Eustachian tube dysfunction with recurrent DME effusion. The subject was totally disabled by his condition and required chronic high doses of prednisone and a blend of gluticasone and salmeterol (Advair®) rescue. Spirometry data was FVC=80% predicted; FEV1=73% predicted. The subject was treated with the sublingual SLO/DNA drops of Example 1 four times daily and three months later the subject was much improved with much less use of rescue inhaler. FVC=96% predicted; FEV1=82% predicted.

After three months a chest x-ray indicated hyperinflated lungs but clear and the next year he was able to begin playing tennis again.

|  | Day 0 | Day 92 |
|---|---|---|
| FVC | 80 | 96 |
| FEV1 | 73 | 82 |

Example 6

According to this example a sixty-two year-old woman presented with COPD/Emphysema/Chronic bronchitis. The subject was a two to three packs per day smoker and suffered from osteoporosis and gallbladder disease and suffered from right lower lobe pneumonia.

On day 0 the subject saw her physician and was desperate for relief. Spirometry data were FEVC=65%; FEV1=47%; $O_2$ Saturation=92%; moderate restrictive and obstructive disease. The subject was treated with the sublingual SLO/DNA drops of Example 1 four times daily in addition to treatment with a blend of gluticasone and salmeterol (Advair®) and tiotropium (Spiriva®).

After five months of treatment on day 149 the subject was still smoking 2 packs per day but had spirometry data of FVC=82%; FEV1=58%; was much better at which point she quit her therapy with the SLO and DNA composition. On day 152 her FVC was down to 69%; FEV1 was down to 48%.

Two more months later the subject was still non-compliant and had spirometry results of FVC=65%; FEV1=41%. Overnight oximetry revealed $O_2$ saturation down to 60-70%. The subject then restarted treatment with the SLO and DNA composition but continued smoking 2-3 packs of cigarettes per day.

Another five months later on day 374 the subject had improved spirometry scores of FVC=79%; FEV1=48%; up from 65% and 41% respectively.

Six months later on day 554 the subject was still smoking 2-3 packs per day and was treated with Spiriva®, Advair®, SLO and DNA and had spirometry data of FVC=77%; FEV1=53%.

|  | Day 1 | Day 149 | Day 152 | Day 221 | Day 374 | Day 554 |
|---|---|---|---|---|---|---|
| FVC | 65 | 82 | 69 | 65 | 79 | 77 |
| FEV1 | 47 | 58 | 48 | 41 | 48 | 53 |

Example 7

According to this example, 30 horses suffering from equine heaves were treated by DNA alone, SLO alone or the combination of DNA and SLO. Two or three horses were treated by administration of SLO alone which had no effect but were then successfully treated by the combination of DNA and SLO. About ten horses were initially treated by administration of DNA alone with some success but improved further when the DNA was combined with SLO. The remaining horses were always treated with the combination of DNA and SLO. Overall, there were positive responses in 75-80% of the subjects.

Numerous modifications and variations in the practice of the invention are expected to occur to those skilled in the art upon consideration of the presently preferred embodiments thereof. Consequently, the only limitations which should be placed upon the scope of the invention are those which appear in the appended claims.

---

What is claimed:

1. A method of inducing bronchodilation or providing relief of bronchospasm in a subject in need thereof comprising the step of:
   administering a composition comprising streptolysin O and DNA in a pharmaceutically-acceptable vehicle to a subject in need thereof wherein the streptolysin O is administered at a dosage of 0.0032 to 50 units per day.

2. The method according to claim 1, wherein said composition is administered sublingually in the form of a liquid drop.

3. The method according to claim 1, wherein the composition is administered in a vehicle selected from the group consisting of water, saline, albumin, or dextrose.

4. The method of claim 1, wherein the streptolysin O consists of amino acid nos. 79-571 of SEQ ID NO: 1.

5. The method of claim 1, wherein said DNA is present in an amount of about 0.00012 mg to about 0.003 mg.

6. The method of claim 1, wherein said DNA is present in an amount of about 0.0003 mg.

7. The method of claim 1, wherein said subject is a human.

8. The method of claim 1, wherein said subject is a horse.

9. The method of claim 1, wherein the subject is suffering from asthma.

10. The method of claim 1, wherein the composition is combined with additional bronchodilator compounds.

* * * * *

SEQUENCE LISTING

```
<160> NUMBER OF SEQ ID NOS: 1

<210> SEQ ID NO 1
<211> LENGTH: 571
<212> TYPE: PRT
<213> ORGANISM: Streptococcus pyogenes

<400> SEQUENCE: 1

Met Ser Asn Lys Lys Thr Phe Lys Lys Tyr Ser Arg Val Ala Gly Leu
1               5                   10                  15

Leu Thr Ala Ala Leu Ile Ile Gly Asn Leu Val Thr Ala Asn Ala Glu
                20                  25                  30

Ser Asn Lys Gln Asn Thr Ala Ser Thr Glu Thr Thr Thr Thr Asn Glu
            35                  40                  45

Gln Pro Lys Pro Glu Ser Ser Glu Leu Thr Thr Glu Lys Ala Gly Gln
        50                  55                  60

Lys Thr Asp Asp Met Leu Asn Ser Asn Asp Met Ile Lys Leu Ala Pro
65                  70                  75                  80

Lys Glu Met Pro Leu Glu Ser Ala Glu Lys Glu Lys Lys Ser Glu
                85                  90                  95

Asp Lys Lys Lys Ser Glu Glu Asp His Thr Glu Glu Ile Asn Asp Lys
            100                 105                 110

Ile Tyr Ser Leu Asn Tyr Asn Glu Leu Glu Val Leu Ala Lys Asn Gly
        115                 120                 125

Glu Thr Ile Glu Asn Phe Val Pro Lys Glu Gly Val Lys Lys Ala Asp
    130                 135                 140

Lys Phe Ile Val Ile Glu Arg Lys Lys Lys Asn Ile Asn Thr Thr Pro
145                 150                 155                 160

Val Asp Ile Ser Ile Ile Asp Ser Val Thr Asp Arg Thr Tyr Pro Ala
                165                 170                 175

Ala Leu Gln Leu Ala Asn Lys Gly Phe Thr Glu Asn Lys Pro Asp Ala
            180                 185                 190

Val Val Thr Lys Arg Asn Pro Gln Lys Ile His Ile Asp Leu Pro Gly
        195                 200                 205

Met Gly Asp Lys Ala Thr Val Glu Val Asn Asp Pro Thr Tyr Ala Asn
    210                 215                 220

Val Ser Thr Ala Ile Asp Asn Leu Val Asn Gln Trp His Asp Asn Tyr
225                 230                 235                 240

Ser Gly Gly Asn Thr Leu Pro Ala Arg Thr Gln Tyr Thr Glu Ser Met
                245                 250                 255

Val Tyr Ser Lys Ser Gln Ile Glu Ala Ala Leu Asn Val Asn Ser Lys
            260                 265                 270

Ile Leu Asp Gly Thr Leu Gly Ile Asp Phe Lys Ser Ile Ser Lys Gly
        275                 280                 285

Glu Lys Lys Val Met Ile Ala Ala Tyr Lys Gln Ile Phe Tyr Thr Val
    290                 295                 300
```

-continued

```
Ser Ala Asn Leu Pro Asn Asn Pro Ala Asp Val Phe Asp Lys Ser Val
305                 310                 315                 320

Thr Phe Lys Glu Leu Gln Arg Lys Gly Val Ser Asn Glu Ala Pro Pro
            325                 330                 335

Leu Phe Val Ser Asn Val Ala Tyr Gly Arg Thr Val Phe Val Lys Leu
            340                 345                 350

Glu Thr Ser Ser Lys Ser Asn Asp Val Glu Ala Ala Phe Ser Ala Ala
            355                 360                 365

Leu Lys Gly Thr Asp Val Lys Thr Asn Gly Lys Tyr Ser Asp Ile Leu
    370                 375                 380

Glu Asn Ser Ser Phe Thr Ala Val Val Leu Gly Gly Asp Ala Ala Glu
385                 390                 395                 400

His Asn Lys Val Val Thr Lys Asp Phe Asp Val Ile Arg Asn Val Ile
            405                 410                 415

Lys Asp Asn Ala Thr Phe Ser Arg Lys Asn Pro Ala Tyr Pro Ile Ser
            420                 425                 430

Tyr Thr Ser Val Phe Leu Lys Asn Asn Lys Ile Ala Gly Val Asn Asn
        435                 440                 445

Arg Thr Glu Tyr Val Glu Thr Thr Ser Thr Glu Tyr Thr Ser Gly Lys
    450                 455                 460

Ile Asn Leu Ser His Gln Gly Ala Tyr Val Ala Gln Tyr Glu Ile Leu
465                 470                 475                 480

Trp Asp Glu Ile Asn Tyr Asp Asp Lys Gly Lys Glu Val Ile Thr Lys
            485                 490                 495

Arg Arg Trp Asp Asn Asn Trp Tyr Ser Lys Thr Ser Pro Phe Ser Thr
            500                 505                 510

Val Ile Pro Leu Gly Ala Asn Ser Arg Asn Ile Arg Ile Met Ala Arg
        515                 520                 525

Glu Cys Thr Gly Leu Ala Trp Glu Trp Trp Arg Lys Val Ile Asp Glu
    530                 535                 540

Arg Asp Val Lys Leu Ser Lys Glu Ile Asn Val Asn Ile Ser Gly Ser
545                 550                 555                 560

Thr Leu Ser Pro Tyr Gly Ser Ile Thr Tyr Lys
            565                 570
```